(12) United States Patent
Bentvelsen et al.

(10) Patent No.: US 10,307,549 B2
(45) Date of Patent: Jun. 4, 2019

(54) AEROSOL GENERATING DEVICE FOR NEBULIZING A LIQUID AND A METHOD OF TEMPERATURE CONTROL OF A LIQUID TO BE NEBULIZED

(75) Inventors: Petrus Henricus Cornelius Bentvelsen, Waalre (NL); Hendrik Huijgen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 522 days.

(21) Appl. No.: 14/000,451

(22) PCT Filed: Feb. 15, 2012

(86) PCT No.: PCT/IB2012/050691
§ 371 (c)(1),
(2), (4) Date: Aug. 20, 2013

(87) PCT Pub. No.: WO2012/114230
PCT Pub. Date: Aug. 30, 2012

(65) Prior Publication Data
US 2013/0327322 A1    Dec. 12, 2013

(30) Foreign Application Priority Data
Feb. 25, 2011    (EP) .................................... 11156036

(51) Int. Cl.
*A61M 11/00*    (2006.01)
*A61M 15/00*    (2006.01)
(Continued)

(52) U.S. Cl.
CPC ...... *A61M 11/005* (2013.01); *A61M 15/0085* (2013.01); *B05B 12/10* (2013.01);
(Continued)

(58) Field of Classification Search
CPC ............ A61M 11/005; A61M 15/0085; A61M 2205/3368; A61M 2205/3382;
(Continued)

(56) References Cited

U.S. PATENT DOCUMENTS 4,210,138 A * 7/1980 Jess ....................... A61M 5/142
                                                 128/DIG. 12
4,632,311 A * 12/1986 Nakane ............... B05B 17/0646
                                                 239/101
(Continued)

FOREIGN PATENT DOCUMENTS

CA         777453 A      2/1968
EP        2216062 A1     8/2010
(Continued)

OTHER PUBLICATIONS

JP 6054761—English Translation.*

*Primary Examiner* — Jan Christopher L Merene
*Assistant Examiner* — Elliot S Ruddie
(74) *Attorney, Agent, or Firm* — Michael W. Haas (57) ABSTRACT

An aerosol generating device (20) comprises a reservoir (1) for containing a liquid to be atomized and a nebulization chamber (3) for nebulizing a portion of the liquid received from the reservoir. The aerosol device further comprises liquid exchange means (7,8) for exchanging in use a further portion of the liquid received in the nebulization chamber with liquid from the reservoir to reduce a temperature increase of liquid in the nebulization chamber caused by heat produced by the piezo (4).

26 Claims, 8 Drawing Sheets

(51) Int. Cl.
*B05B 12/10* (2006.01)
*B05B 17/00* (2006.01)
*B05B 17/06* (2006.01)

(52) U.S. Cl.
CPC ...... *B05B 17/0646* (2013.01); *B05B 17/0676* (2013.01); *A61M 2205/3368* (2013.01); *A61M 2205/3382* (2013.01); *A61M 2205/3606* (2013.01)

(58) Field of Classification Search
CPC ...... A61M 2205/3606; A61M 16/1075; A61M 16/108; A61M 16/1085; A61M 16/109; A61M 2205/3306; B05B 12/10; B05B 17/0646; B05B 17/0676; B05B 17/06; B05B 17/0607; B05B 17/0615; B05B 17/0638; B05B 5/00; B05B 5/001; B05B 3/00; B05B 3/001; B05B 7/02; B05B 7/16; B05B 7/168; B05B 9/002; B05B 11/0002; B05B 7/1633
USPC ........... 128/200.14, 200.16, 200.18, 200.21, 128/200.23, 203.12, 203.16, 128/203.25–203.27; 239/102.1; 601/2
See application file for complete search history.

(56) References Cited

U.S. PATENT DOCUMENTS

| | | | |
|---|---|---|---|
| 4,776,990 A * | 10/1988 | Verity | B05B 7/162 128/200.16 |
| 5,312,281 A * | 5/1994 | Takahashi | A63H 17/34 239/102.2 |
| 5,388,571 A | 2/1995 | Roberts et al. | |
| 5,743,251 A | 4/1998 | Howell et al. | |
| 6,085,740 A | 7/2000 | Irvi et al. | |
| 6,158,431 A | 12/2000 | Poole | |
| 6,405,934 B1 | 6/2002 | Hess | |
| 6,883,729 B2 | 4/2005 | Putvinski et al. | |
| 7,034,436 B2 * | 4/2006 | Chemisky | F02D 41/2096 310/315 |
| 7,201,163 B2 * | 4/2007 | Jiang | A61M 16/1075 128/200.14 |
| 2003/0131844 A1 * | 7/2003 | Kumar | A61K 33/00 128/200.24 |
| 2003/0215514 A1 | 11/2003 | Platz | |
| 2005/0016380 A1 * | 1/2005 | Matsuura | B01D 3/06 96/389 |
| 2008/0072899 A1 | 3/2008 | Niland et al. | |
| 2008/0230052 A1 * | 9/2008 | Montaser | A61M 15/0085 128/200.16 |
| 2009/0101814 A1 | 4/2009 | Amirav | |

FOREIGN PATENT DOCUMENTS

| | | | | |
|---|---|---|---|---|
| JP | 60054761 | | 3/1985 | |
| JP | 61097066 | | 5/1986 | |
| JP | H07302747 A | | 11/1995 | |
| JP | 2003029849 A | | 1/2003 | |
| JP | 2004290426 A | | 10/2004 | |
| JP | 2005102899 A | | 4/2005 | |
| JP | 2008539890 A | | 11/2008 | |
| JP | 2009172596 | | 6/2009 | |
| JP | 2009172596 A | * | 8/2009 | ............. B01J 19/10 |
| JP | 2010505540 A | | 2/2010 | |
| WO | WO0012278 A1 | | 3/2000 | |
| WO | WO2006083511 A2 | | 8/2006 | |
| WO | WO2008042912 A2 | | 4/2008 | |

* cited by examiner

FIG. 8

AEROSOL GENERATING DEVICE FOR NEBULIZING A LIQUID AND A METHOD OF TEMPERATURE CONTROL OF A LIQUID TO BE NEBULIZED

CROSS-REFERENCE TO PRIOR APPLICATIONS

This application is the U.S. National Phase application under 35 U.S.C. § 371 of International Application Serial No. PCT/IB2012/050691, filed on Feb. 15, 2012, which claims the benefit of European Application Serial No. 11156036.3, filed on Feb. 25, 2011. These applications are hereby incorporated by reference herein.

TECHNICAL FIELD OF THE INVENTION

The invention relates to an aerosol generating device for nebulizing a liquid. Such an aerosol device may for example be used for nebulizing a drug for inhalation by a patient whereby the nebulized drug is administered to the patient through deposition in his lungs. The invention further relates to a method of temperature control of a liquid to be nebulized. The liquid may for example be a drug.

BACKGROUND OF THE INVENTION

Several different types of nebulizers are known such as for example ultrasonic type nebulizers which use a piezo electric crystal to atomize the liquid received in a nebulization chamber using a mesh. The piezo electric crystal may for example be used to vibrate the mesh causing the liquid to be dispersed through the mesh to form a spray of small droplets. In another example the piezo electric crystal is used to vibrate the liquid in the nebulization chamber causing it to be nebulized through the mesh. The temperature of some liquids, such as for example drugs, must be kept within specified limits. Due to efficiency limitations the piezo electric crystal will transform part of the electrical energy offered at its terminals to mechanical movement and another part to heat. As the piezo electric crystal is in direct or indirect contact with the liquid that is received in the nebulization chamber the heat produced by the piezo electric crystal may cause a temperature rise of the liquid. It is an object of the invention to reduce a temperature rise of the liquid in the nebulization chamber.

SUMMARY OF THE INVENTION

The object is achieved with the aerosol generating device for nebulizing a liquid according to claim 1. The liquid in the nebulizing chamber is received from the reservoir and brought into vibration by the vibration means. Due to limitations in the efficiency the vibration means will produce heat causing the temperature of the nebulization chamber and the liquid contained therein to increase. To limit this temperature increase a further portion of the liquid received in the nebulization chamber is exchanged with liquid from the reservoir. The liquid in the reservoir is not affected by the heat generated by the vibration source and has therefore a lower temperature than the portion of the liquid that is contained in the nebulization chamber. By exchanging the further portion of the liquid with the liquid contained in the reservoir the temperature rise of the portion of the liquid contained in the nebulization chamber is limited and the temperature of the liquid contained in the nebulization chamber is reduced.

In an embodiment the volume of the nebulization chamber is in the range of 0.1 ml to 0.2 ml and the sum of the volumes of the nebulization chamber and the reservoir is in the range of 0.25 ml to 1.75 ml. In another embodiment the volume of the reservoir is at least 5 times larger than the volume of the nebulization chamber.

In an embodiment the aerosol generating device is arranged for filling the reservoir from an external source such as a vial. In a further embodiment the aerosol generating device comprises a further reservoir for metering the liquid received from an external source, the reservoir being arranged to receive a metered liquid dose from the further reservoir.

In a further embodiment the mesh is mounted across an aperture in the nebulization chamber, the vibration source being arranged to vibrate the mesh. The vibrations of the mesh causes the liquid contained in the nebulization chamber to pass through the holes in the mesh forming droplets which are released from the front surface of the mesh.

In a further embodiment the nebulization chamber is constructed to form a gap between the mesh and the vibration source. The portion of the liquid that is received in the nebulization chamber is fed into the space between the mesh and the vibration source. The vibration source causes pressure waves in the liquid contained in the space causing the liquid to pass through the holes in the mesh thereby forming a spray of droplets.

The exchange means for exchanging liquid between the reservoir and the nebulization chamber may comprise for example a channel, or a pump, or both. The liquid exchange may for example result from capillary or gravity force. In a further embodiment the reservoir and the nebulization chamber are positioned relative to each other to allow in use the nebulization chamber to be filled as a result of the gravity force. The reservoir may be interfacing with the nebulization chamber and may have an aperture in the wall where the reservoir and nebulization chamber interface to allow the nebulization chamber to be filled with the portion of the liquid from the reservoir through said aperture. To support the exchanging the exchange means may further comprise a return channel for feeding the further portion from the nebulization chamber to the reservoir.

In a further embodiment the exchange means include an active component such as for example a pump wherein the pump is controlled in dependence of a measured temperature of the liquid in the nebulization chamber. When the measured temperature is above a predetermined threshold the pump is activated to flush the liquid contained in the nebulization chamber. In a further embodiment the aerosol generating device may further comprise temperature sensing means to measure a temperature of the liquid contained in the reservoir or nebulization chamber. Due to the nebulizing of the liquid contained in the nebulization chamber the total volume of liquid in the nebulization chamber and the reservoir decreases. This will cause a temperature rise of the liquid contained in the reservoir and nebulization chamber. If the temperature of the liquid contained in the reservoir or nebulization chamber is above a predetermined threshold the nebulizing may be stopped, paused or continued at a reduced power level such that the heat produced by the nebulizing means is reduced. In a further embodiment the liquid exchange means may further comprise cooling means. These cooling means may for example be passive such as a heat sink coupled to a return channel. The cooling means may also be active such a Peltier element which for example may be operated in dependence of a measured liquid temperature in the nebulization chamber and/or reservoir.

The object is further achieved with a method of temperature control of a liquid to be nebulized in an aerosol generating device according to claim 12.

BRIEF DESCRIPTION OF THE DRAWINGS

Specific embodiments of the invention will now be described, by way of example only, with reference to the following drawings, in which.

DETAILED DESCRIPTION OF THE EMBODIMENTS

Figure 1:
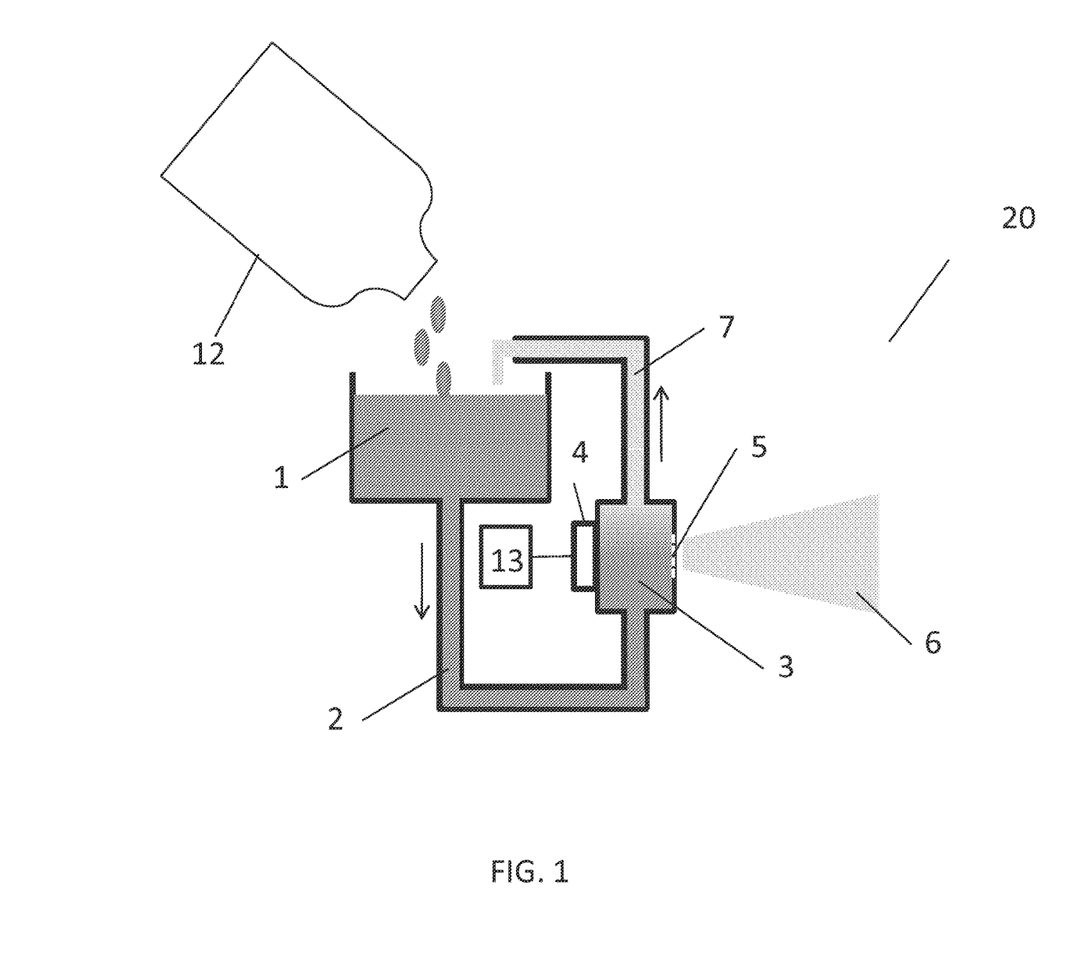
FIG. 1 shows an embodiment of an aerosol generating device.
Figure 2A:
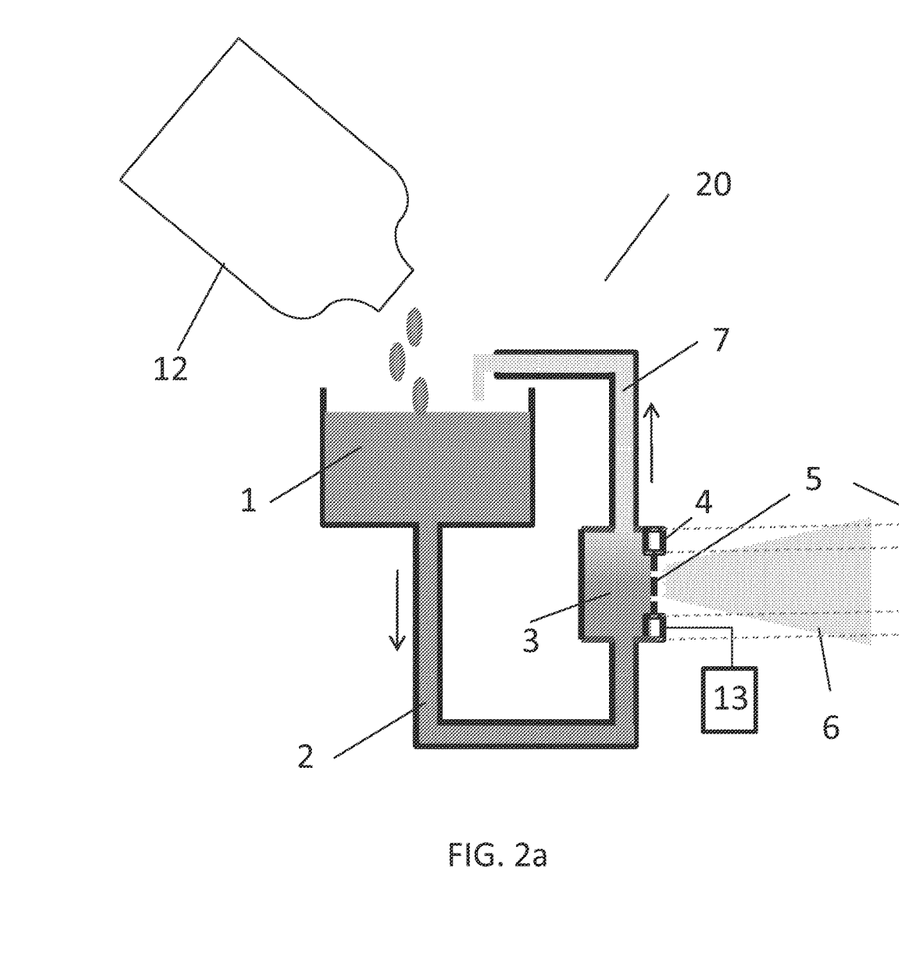
FIG. 2a shows a further embodiment of an aerosol generating device.
Figure 2B:
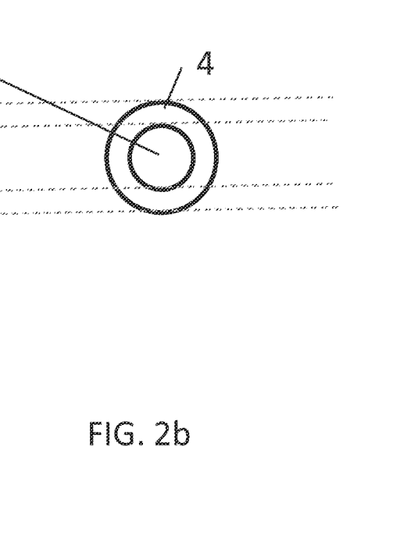
FIG. 2b shows an embodiment of a vibration means coupled to a mesh.
Figure 3:
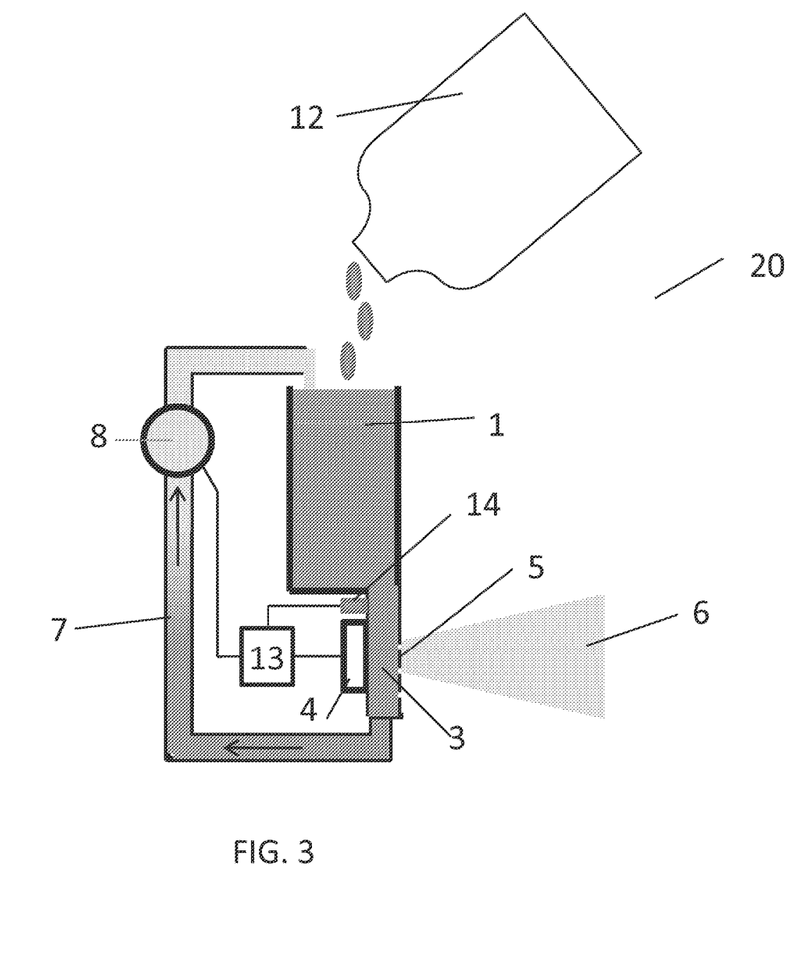
FIG. 3 shows a further embodiment of an aerosol generating device comprising one return channel and pumping means.
Figure 4:
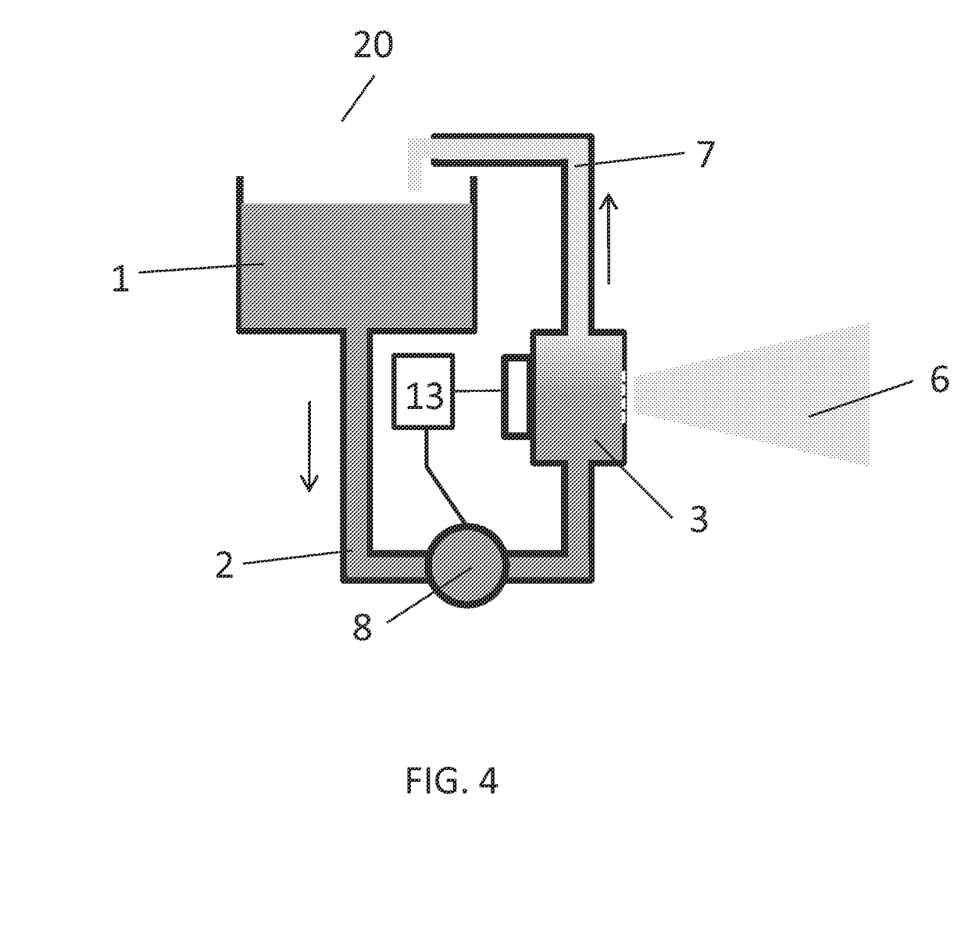
FIG. 4 shows a further embodiment of an aerosol generating device comprising pumping means in the supply channel.
Figure 5:
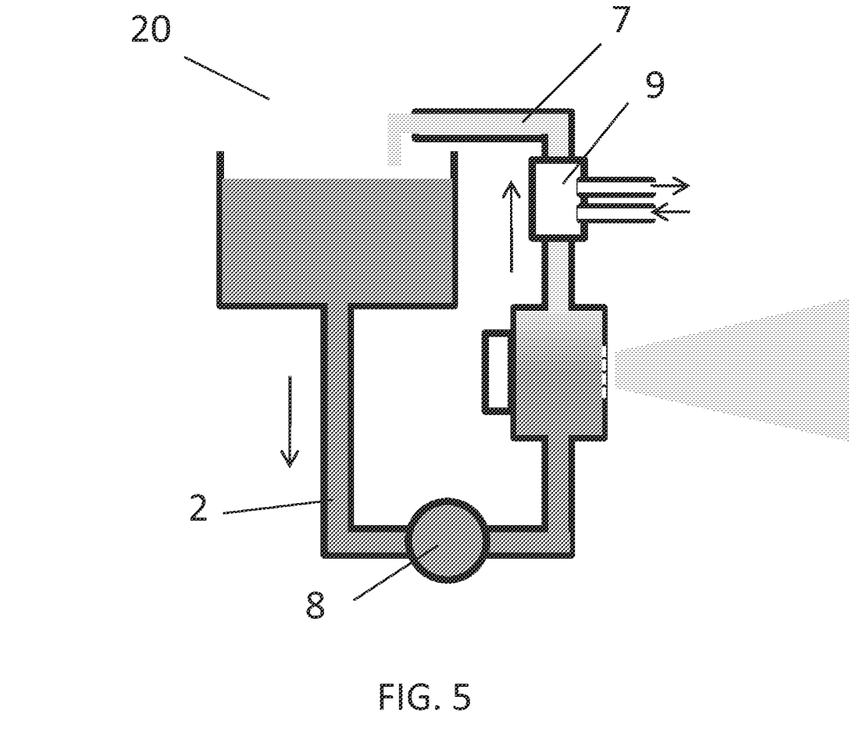
FIG. 5 shows an embodiment of an aerosol generating device comprising cooling means.
Figure 6:
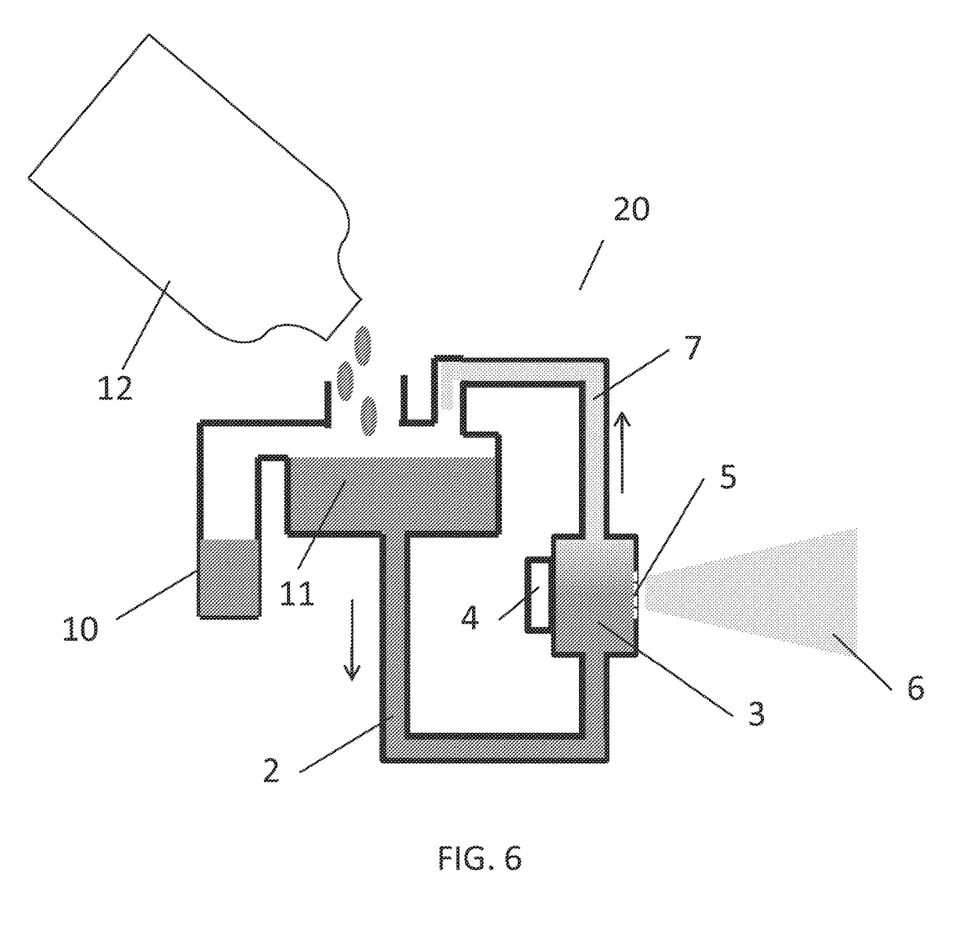
FIG. 6 shows an embodiment of an aerosol generating device with a metering chamber.
Figure 7:
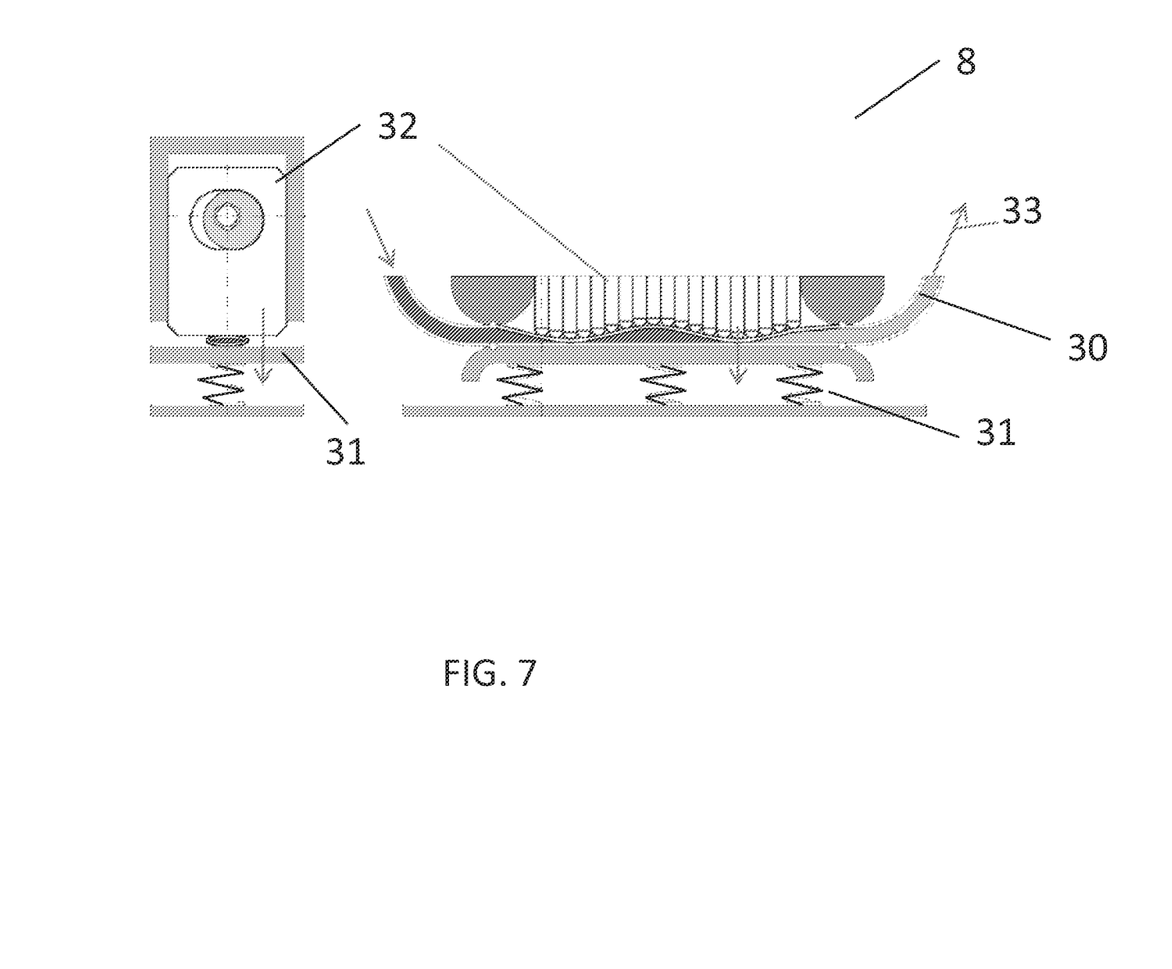
FIG. 7 shows an embodiment of pumping means.

FIGS. 1-6 show embodiments of an aerosol generating device comprising a reservoir 1, a nebulization chamber 3 and liquid exchanging means 2, 7, 8 coupled between the nebulization chamber and the reservoir. The liquid exchange means supplies in use a portion of a liquid from the reservoir to the nebulization chamber and exchanges a further portion of the liquid received in the nebulization chamber with liquid from the reservoir. FIG. 1 shows an aerosol generating device 20 or nebulizer having a mesh 5 mounted across an aperture in the nebulization chamber 3. The mesh is realized by for example thin metal plate with small holes. A vibration means 4 such as a piezo electric element is coupled to the nebulization chamber such that in operation its produced heat and vibrations are transferred to the liquid contained in the nebulization chamber. FIG. 2a shows a further embodiment of a nebulizer 20 in which the vibration means 4 is coupled to the nebulization chamber 3. In this embodiment the vibration means is for example an O-ring shaped piezo electric element. The piezo is connected to the mesh 5 see FIG. 2b showing a front side view, wherein the mesh may have a concave shape. During a vibrational motion of the piezo pressure is built up in the vicinity of the mesh causing an ejection of the fluid through the holes as droplets and creating an aerosol. In both shown embodiments of FIGS. 1 and 2 the liquid to be atomized into an aerosol 6 is driven through the holes of the mesh 5 by the vibration of the piezo 4. The heat produced in the piezo will cause a temperature rise of the liquid contained in the nebulization chamber 3. In an embodiment the volume of the nebulization chamber 3 is in the range of 0.1 ml to 0.2 ml and the sum of the volumes of the reservoir 1 and the nebulization chamber is in the rage of 0.25 ml to 0.75 ml. The nebulization output rate resulting in spray 6 may for example be in the range of 0.25 ml/minute to 1.5 ml/minute. With an output rate of 0.25 ml/minute and a sum of the volumes of reservoir and the nebulization chamber of 0.75 ml the nebulizing of the fluid takes about 3 minutes. During these 3 minutes the dissipation of the piezo will cause a temperature rise of the liquid, and thus also of the spray 6. This temperature rise may for some liquids such as drugs be undesirable. The produced heat can be decreased by operating the vibration means 4 at a lower power level at the cost of a reduced output flow of the spray 6. The power level at which the piezo is operating is controlled by a controller 13 which may determine a frequency, a duty cycle and voltage level at which the piezo is driven. The nebulizer 20 further comprises a reservoir 1 that is coupled via a supply channel 2 to the nebulization chamber. The reservoir may for example be filled by the user with a medicine from a drug vial 12. In another embodiment the volume of the drug to be delivered to the patient's lungs is equal to the sum of the volumes of the reservoir and the nebulization chamber. As the volume in the vial may be larger than the volume of the reservoir 1 an overflow chamber 10 may be added such as shown in the embodiment of FIG. 6 in which the reservoir has the function of a metering chamber 11 with a volume corresponding to a treatment. In a further embodiment, not shown, the nebulizer may have a metering chamber and overflow chamber for metering the volume of the drug and a reservoir arranged for receiving the metered volume from the metering chamber. It is preferred that the volume of the reservoir is larger than the volume of the nebulization chamber. In operation of the nebulizer the nebulization chamber 3 is filled with a portion of the liquid contained in the volume of the reservoir 1. The supply channel 2 coupling the reservoir 1 to the chamber 3 may be dimensioned to provide a capillary filling of the nebulization chamber. FIG. 1 shows the aerosol device 20 being constructed to obtain that in use the reservoir 1 is positioned above the nebulization chamber 3 such that the gravity force causes a liquid flow from the reservoir 1 to the chamber 3. FIG. 3 shows an embodiment of an aerosol device 20 in which the reservoir 1 and nebulization chamber 3 are coupled without a supply channel. In use the heat produced by the vibration source 4 is transferred to the liquid contained in the chamber 3 causing a temperature rise. To obtain a reduction of the temperature of the liquid in the nebulization chamber 3 a liquid exchange between the nebulization chamber and the reservoir 1 is realized. The liquid exchange may for example be realized by pumping a further portion of the liquid contained in the nebulization chamber 3 back to the reservoir 1 and refill the nebulization chamber with liquid from the reservoir such that the average temperature of the liquid contained in the nebulization chamber is reduced. In FIG. 3 the liquid exchange means comprise a return channel 7 with a pump 8. The operation of the pump may for example be dependent on the controller 13 such as shown in FIG. 3. When the controller 13 drives the piezo 4 above a predetermined power level the pump 8 is activated, and the pump may remain being activated a predetermined time after the piezo has stopped being driven (and the nebulizing has been halted or paused) to allow a flushing of the liquid contained in the nebulization chamber 3. The nebulizer 20 may further comprise temperature sensing means 14, see FIG. 3, wherein the operation of the pump 8 by the controller 13 is further in dependence of the temperature of the liquid in the nebulization chamber 3 and/or reservoir 1. Also the power level at which the vibration means 4 is operated may be adjusted by the controller 13 in response to the measured temperature. Continuing with the embodiment shown in FIG. 4, the pumping means 8 may also be provided in the supply channel 2. This embodiment has the advantage of providing more freedom in the positioning of the reservoir 1 relative to the nebulization chamber 3 as the filling of the chamber can be made independent of gravity. In case the temperature decrease by the liquid exchange between the nebulization chamber and the reservoir is insufficient cooling means 9 may be included in the nebulizer 20. FIG. 5 shows an embodiment in which cooling means 9 have been added to the return channel 7. Cooling means may be active such as with a Peltier element or use a cool fluid, or be passive such as with a heat sink. In an embodiment the surface area of the return channel 7 is enlarged with a heat sink to allow an improved heat exchange with the surrounding material or air. In a further embodiment, not shown in a Figure, the shape and inner surface area of the walls of the reservoir are adapted to maximize its contact area with the fluid contained in the reservoir to optimize a heat exchange between the fluid and the material of the reservoir. The reservoir comprises preferably made a material with a low specific heat such as for example copper. The reservoir may further be coupled to a heat conductor adapted to transport the heat to an area where it can easily exchange the transported heat with the ambient air surrounding the nebulizer. In a further embodiment, not shown in a Figure, a fluid sensor is located between the reservoir and the nebulization chamber such that, once the liquid to be atomized has almost all been aerosolized, this is detected by the controller and the pumping means and vibration means are switched off. FIG. 7 shows an example of a pumping means 8 which comprises of a plurality of moving elements 32 such as shown in the left figure of FIG. 7. The plurality of moving elements 32, see right figure of FIG. 7, press successively on a flexible tube or channel 30 which is clamped between the plurality of moving elements and a resilient member 31 to create a peristaltic like movement resulting in a fluid flow 33. The fluid is not in direct contact with the pump 8 which has the advantage that the pump does not need to be cleaned regularly. For hygiene the flexible tube 30 may be cleaned or replaced after use of the nebulizer.

Figure 8:
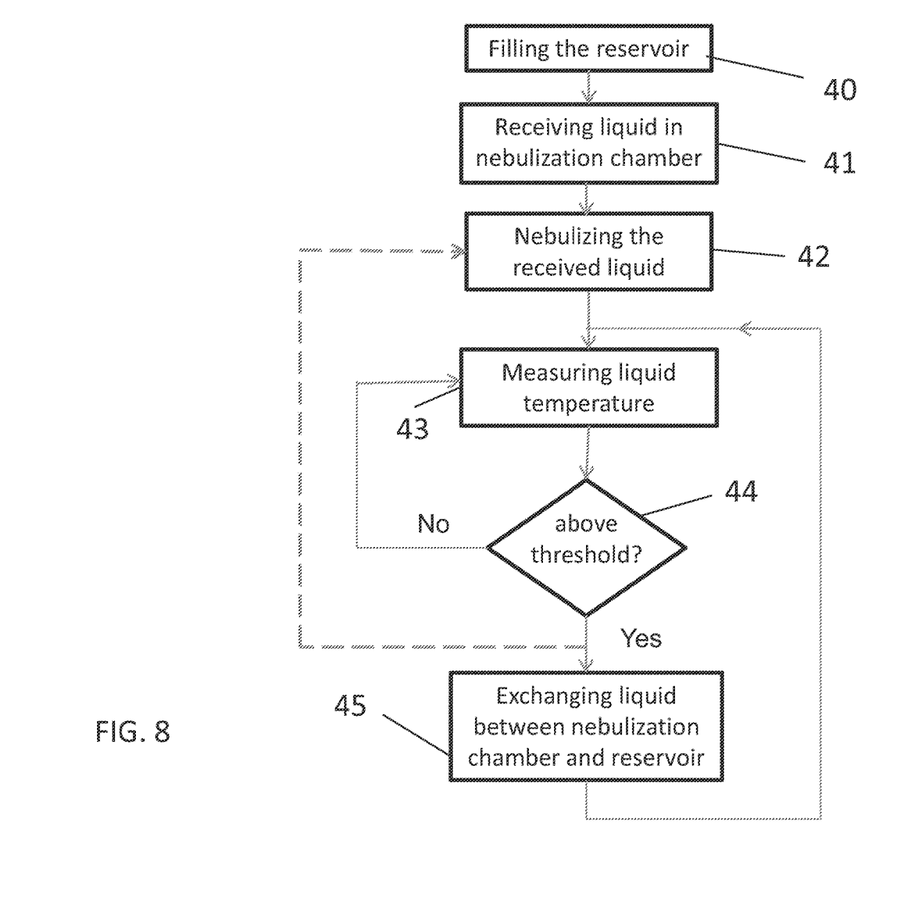
FIG. 8 shows an embodiment of a method of temperature control of a liquid to be nebulized in an aerosol generating device.

FIG. 8 shows an embodiment of a method of temperature control of a liquid to be nebulized in an aerosol generating device 20. The method comprises the step of filling 40 the reservoir 1 with a drug. This may be a metered volume corresponding to a treatment. After or during the filling of the reservoir 1 in a next step 41 a portion of the liquid is received in the nebulization chamber 3 which is arranged to nebulize the liquid received therein. Subsequently in step 42 after activation of the nebulizer 20 by the patient the controller 13 activates the vibration means 4 causing the generation of a spray 6 of small droplets. Part of the energy supplied to the vibration means 4 is dissipated as heat. During the nebulizing in a next step 43 of the method the temperature of the liquid in the nebulization chamber 3 is measured with a sensor 14. The controller 13 compares the measured temperature with a predetermined threshold in step 44. In case the temperature is higher than said threshold the controller 13 activates in a subsequent step 45 a pumping means 8 to exchange liquid between the nebulization chamber and reservoir until the temperature of the liquid in the nebulization chamber 3 has dropped below the predetermined threshold. In a further embodiment of the method the controller 13 reduces the power level with which the vibration means 4 is driven if the measured liquid temperature has increased above a further predetermined threshold as illustrated by the dashed line in FIG. 8. In another embodiment there is no step of measuring liquid temperature and is the exchange of the liquid between the nebulization chamber and the reservoir started when the patient activates the nebulizer.

Summarizing in the invention an aerosol generating device 20 comprises a reservoir 1 for containing a liquid to be atomized and a nebulization chamber 3 for nebulizing a portion of the liquid received from the reservoir. The aerosol device further comprises liquid exchange means 7,8 for exchanging in use a further portion of the liquid received in the nebulization chamber with liquid from the reservoir to reduce a temperature increase of liquid in the nebulization chamber caused by heat produced by the vibration source 4.

While the invention has been illustrated and described in detail in the drawings and foregoing description, such illustration and description are to be considered illustrative or exemplary and not restrictive; the invention is not limited to the disclosed embodiments. Variations to the disclosed embodiments can be understood and effected by those skilled in the art in practicing the claimed invention, from a study of the drawings, the disclosure, and the appended claims. For example in the embodiments described above the vibration means causes a pressure wave in the liquid causing the liquid to pass through the mesh to form a spray of small droplets. The invention also applies to nebulizers with other arrangements in which a vibration means is used to cause directly or indirectly a vibration of a mesh or nozzle plate and in which the heat produced by the vibration means causes a temperature increase of the spray of nebulized droplets.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An aerosol generating device for nebulizing a liquid, the device comprising:
   a reservoir;
   a nebulization chamber being arranged for receiving in use a portion of a liquid from the reservoir;
   a vibration means coupled to the nebulization chamber and arranged for bringing the portion of the liquid in vibration;
   liquid exchange means for exchanging in use a further portion of the liquid received in the nebulization chamber with liquid from the reservoir, wherein the liquid exchange means comprises at least one channel providing fluid communication between the reservoir and the nebulization chamber; and
   temperature sensing means arranged for measuring a temperature of the liquid contained in the nebulization chamber and/or the reservoir;
   wherein the device is further configured, responsive to the temperature sensing means indicating the measured temperature is above a predetermined threshold, to operate at least one of:
   (i) an active component in the liquid exchange means based on the measured temperature; or
   (ii) the vibration means at a decreased power level determined based on the measured temperature.

2. An aerosol generating device according to claim 1 wherein the liquid exchange means comprises a supply channel for feeding in use the portion of liquid from the reservoir to the nebulization chamber and a return channel for feeding the further portion of the liquid from the nebulization chamber to the reservoir.

3. An aerosol generating device according to claim 1 comprising the active component, wherein the active component in the liquid exchange means comprises pumping means.

4. An aerosol generating device according to claim 3 wherein the pumping means is arranged to operate based on a controlling of the vibration means.

5. An aerosol generating device according to claim 3, wherein the channel comprises a flexible tube, wherein the pumping means comprises a plurality of moving elements disposed on the channel, wherein individual ones of the plurality of moving elements are configured to press successively on the channel to create a peristaltic movement.

6. An aerosol generating device according to claim 1 further comprising cooling means for reducing the temperature of the further portion of the liquid, the cooling means being arranged in the at least one channel to cool the further portion of the liquid, wherein the device is further configured, responsive to the temperature sensing means indicating the measured temperature is above the predetermined threshold, to operate:
  (i) the active component in the liquid exchange means based on the measured temperature;
  (ii) the vibration means at the decreased power level determined based on the measured temperature; and
  (iii) the cooling means based on the measured temperature.

7. An aerosol generating device according to claim 6, wherein the cooling means comprises a heat sink and wherein a surface area of a portion of the channel is enlarged by the heat sink.

8. An aerosol generating device according to claim 6, wherein the cooling means comprises a Peltier element.

9. An aerosol generating device according to claim 1 wherein the nebulization chamber is arranged such that the liquid is received in a space between the vibration means and a mesh, wherein the vibration means is arranged to bring the liquid comprised in said space in vibration, the mesh having a plurality of orifices for dispersing another portion of the liquid received in the nebulization chamber as a spray of small droplets as a result of the vibration.

10. An aerosol generating device according to claim 9 wherein in use a height difference in the relative positioning of the reservoir and the nebulization chamber causes a liquid flow from the reservoir to the nebulization chamber as a result of gravity.

11. An aerosol generating device according to claim 10 wherein the reservoir comprises a metering chamber and an overflow chamber, the metering chamber defining the volume of the liquid to be nebulized, the metering chamber being arranged such that the liquid is poured into the metering chamber from outside the nebulizer and any liquid in excess of the volume being retained in the overflow chamber, the nebulization chamber being arranged for receiving the portion of the liquid from the metering chamber, the aerosol generating device being arranged for exchanging the further portion of the liquid between the metering chamber and the nebulization chamber.

12. An aerosol generating device according to claim 1, wherein the device is further configured, responsive to the temperature sensing means indicating the measured temperature is above the predetermined threshold, to operate the vibration means at the decreased power level determined based on the measured temperature but not the active component.

13. A method of temperature control of a liquid to be nebulized in an aerosol generating device, the aerosol generating device comprising a nebulization chamber for nebulizing a portion of the liquid received from a reservoir, the method comprising:
  filling the reservoir with the liquid;
  receiving the portion of the liquid in the nebulization chamber;
  controlling a vibration means to control the nebulizing of the portion of the liquid;
  exchanging a further portion of the liquid received in the nebulization chamber between the reservoir and the nebulization chamber, and
  measuring a temperature of the liquid contained in the nebulization chamber and/or the reservoir;
  wherein, responsive to the measured temperature being above a predetermined threshold, the method further comprises:
    (i) exchanging the further portion, through at least one channel, based on the measured temperature; and/or
    (ii) controlling the vibration means at a decreased power level determined based on the measured temperature.

14. A method according to claim 13 wherein the step of exchanging the further portion is further based on the controlling of the vibration means.

15. A method according to claim 13 wherein the step of exchanging includes generating a liquid flow from the nebulization chamber via a return channel to the reservoir.

16. A method according to claim 15, wherein generating the liquid flow comprises creating, via a plurality of moving elements disposed on the return channel, a peristaltic movement by pressing individual ones of the plurality of moving elements successively on the channel.

17. A method according to claim 13, wherein, responsive to the measured temperature being above the predetermined threshold, the method further comprises:
  (i) exchanging the further portion, through the at least one channel, based on the measured temperature;
  (ii) controlling the vibration means at the decreased power level determined based on the measured temperature; and
  (iii) operating cooling means based on the measured temperature, the cooling means being arranged in the at least one channel to cool the further portion of the liquid, the at least one channel providing fluid communication between the nebulization chamber and the reservoir.

18. A method according to claim 17, wherein the cooling means comprises a heat sink and wherein a surface area of a portion of the channel is enlarged by the heat sink.

19. A method according to claim 17, wherein the cooling means comprises a Peltier element.

20. A method according to claim 13, wherein, responsive to the measured temperature being above the predetermined threshold, the method further comprises controlling the vibration means at a decreased power level determined based on the measured temperature but not exchanging the further portion, through the at least one channel, based on the measured temperature.

21. An aerosol generating device for nebulizing a liquid, the device comprising:
  a reservoir;
  a nebulization chamber arranged for receiving in use a portion of a liquid from the reservoir;

a piezoelectric element coupled to the nebulization chamber and arranged for bringing the portion of the liquid in vibration;

channels and a pump configured to exchange, in use, a further portion of the liquid received in the nebulization chamber with liquid from the reservoir; and one or more temperature sensors arranged to measure a temperature of the liquid contained in the nebulization chamber and/or the reservoir;

wherein the device is further configured, responsive to the one or more temperature sensors indicating the measured temperature is above a predetermined threshold, to operate at least one of:

(i) the pump based on the measured temperature; or (ii) the piezoelectric element at a decreased power level determined based on the measured temperature.

22. An aerosol generating device according to claim 21, wherein the channels comprise a flexible tube, wherein the pump comprises a plurality of moving elements disposed on the channel, wherein individual ones of the plurality of moving elements are configured to press successively on the channel to create a peristaltic movement.

23. An aerosol generating device according to claim 21, further comprising cooling means for reducing the temperature of the further portion of the liquid, the cooling means being arranged in the at least one channel to cool the further portion of the liquid, wherein the device is further configured, responsive to the one or more temperature sensors indicating the measured temperature is above the predetermined threshold, to operate:

(i) the pump based on the measured temperature;

(ii) the piezoelectric element at the decreased power level determined based on the measured temperature; and (iii) the cooling means based on the measured temperature.

24. An aerosol generating device according to claim 23, wherein the cooling means comprises a heat sink and wherein a surface area of a portion of the channel is enlarged by the heat sink.

25. An aerosol generating device according to claim 23, wherein the cooling means comprises a Peltier element.

26. An aerosol generating device according to claim 21, wherein the device is further configured, responsive to the one or more temperature sensors indicating the measured temperature is above a predetermined threshold, to operate the piezoelectric element at the decreased power level determined based on the measured temperature but not the pump.

* * * * *